(12) United States Patent
Vidal et al.

(10) Patent No.: US 10,639,066 B2
(45) Date of Patent: May 5, 2020

(54) SYSTEM FOR CONTROLLING DISPLACEMENT OF AN INTERVENTION DEVICE

(71) Applicant: ENDOCONTROL, La Tronche (FR)

(72) Inventors: Clement Vidal, Grenoble (FR); Berengere Bardou, Grenoble (FR)

(73) Assignee: US Patent Innovations, LLC, Takoma Park, MD (US)

(*) Notice: Subject to any disclaimer, the term of this patent is extended or adjusted under 35 U.S.C. 154(b) by 369 days.

(21) Appl. No.: 15/518,452

(22) PCT Filed: Oct. 14, 2014

(86) PCT No.: PCT/IB2014/002247
§ 371 (c)(1),
(2) Date: Apr. 11, 2017

(87) PCT Pub. No.: WO2016/059445
PCT Pub. Date: Apr. 21, 2016

(65) Prior Publication Data
US 2017/0303957 A1 Oct. 26, 2017

(51) Int. Cl.
*A61B 17/34* (2006.01)
*A61B 90/11* (2016.01)
*A61B 17/00* (2006.01)

(52) U.S. Cl.
CPC .......... *A61B 17/3403* (2013.01); *A61B 90/11* (2016.02); *A61B 2017/00265* (2013.01);
(Continued)

(58) Field of Classification Search
CPC ...... A61B 17/3403; A61B 2017/00265; A61B 2017/3405; A61B 2017/3047; A61B 90/11
See application file for complete search history.

(56) References Cited

U.S. PATENT DOCUMENTS 4,592,352 A 6/1986 Patil
5,163,430 A 11/1992 Carol
(Continued)

FOREIGN PATENT DOCUMENTS

WO WO 2009107922 A1 9/2009

OTHER PUBLICATIONS

International Search Report in PCT/IB2014/002247 dated Jul. 3, 2015.

*Primary Examiner* — Sarah A Simpson

(57) ABSTRACT

A system for controlling displacement of an intervention device having an end for inserting in a patient body, including a base in a fixed position relative to the patient. A first portion has an arc member and is pivotally mounted on the base around a first axis (A1). A second portion includes a support member and a carrier member. The support member partially rotates around a second axis (A2). A third portion includes a holding member, and a sliding member mounted on the support member along a translation axis ($A_T$). The holding member is arranged so that translation of the sliding member causes the intervention device to translate along a third axis (A3). The third axis (A3) is parallel to and offset from the translation axis ($A_T$). When the carrier member is positioned halfway of the arc member, the first (A1), second (A2) and third (A3) axes are orthogonal.

20 Claims, 5 Drawing Sheets

(52) U.S. Cl.
CPC ............... *A61B 2017/3405* (2013.01); *A61B 2017/3409* (2013.01)

(56) References Cited

U.S. PATENT DOCUMENTS

| | | | |
|---|---|---|---|
| 5,984,930 | A | 11/1999 | Maciunas et al. |
| 6,283,977 | B1 | 9/2001 | Ericsson et al. |
| 8,591,397 | B2 | 11/2013 | Berkelman et al. |
| 2002/0007188 | A1 | 1/2002 | Arambula et al. |
| 2004/0220588 | A1* | 11/2004 | Kermode ............ A61B 10/0041 606/129 |
| 2008/0091066 | A1* | 4/2008 | Sholev ............... A61B 1/00016 600/112 |
| 2008/0269777 | A1* | 10/2008 | Appenrodt ........... A61N 1/0529 606/130 |
| 2008/0275466 | A1 | 11/2008 | Skakoon |
| 2011/0040304 | A1 | 2/2011 | Li et al. |

* cited by examiner

SYSTEM FOR CONTROLLING DISPLACEMENT OF AN INTERVENTION DEVICE

FIELD OF THE INVENTION

The invention relates to a system for controlling displacement of an intervention device used during a surgery, in particular for minimally invasive surgery.

TECHNICAL BACKGROUND

Within the scope of minimally-invasive surgery, such as endoscopic or laparoscopic surgery, access to the operating site is made via small incisions in the body of the patient (such as the abdomen or thorax), in which the practitioner places a cannula formed by a tube whereof the diameter typically varies from 3 to 15 mm, through which the practitioner can insert into the body of the patient either an endoscope for obtaining a video image on a monitor, or long and fine instruments for performing a procedure at the operating site.

In some cases or for some specific intervention devices, access is made through a natural orifice, e.g. vagina when the intervention device is a uterine manipulator. Indeed a uterine manipulator is a device inserted in the uterus through the vagina and cervix to position the patient uterus without making a specific incision in the patient skin.

Manipulation of an intervention device through small incisions or through a natural orifice requires in both cases to move it around a fixed point or center of motion, which corresponds to the incision or natural orifice itself. Such incision or natural orifice is herein generally referred as a point of penetration in the patient.

Since the surgeon generally has both hands occupied by the surgical instruments, an assistant is necessary to maintain any other intervention device in a desired position, in particular the endoscope that is used to guide the surgeon in his surgery.

Robotic systems have been developed to handle and displace the endoscope in the place of the assistant. Such systems are generally formed of massive, complex, and expensive robots comprising a base attached to the ground and an arm handling the endoscope. In the limited space of an operation room, the base of such a robot takes up a considerable space close to the patient. Further, the arm of the robot maintaining the endoscope may hinder the access to the patient's abdomen.

Alternative solutions have thus been proposed consisting in holders designed to hold and move an intervention device, e.g. an endoscope, during surgeries. Such systems are much more compact and easy to use for the surgeon.

An example of such system is for instance described in U.S. Pat. No. 8,591,397 published on Nov. 26, 2013 that discloses a compact motorized endoscope holder placed directly on the patient's abdomen. More precisely, the motorized endoscope holder is formed of a base attached to a passive arm, a ring portion rotatably assembled on the base according to an axis perpendicular to said base, a longitudinal portion rotatably assembled on the ring portion according to an axis perpendicular to and intersecting the first axis, and a holding portion slidably assembled on the second portion along a translation axis intersecting the first two rotation axes at the same point. It further comprises electrical motors for actuating the ring portion with respect to the base, the longitudinal portion with respect to the ring portion and holding portion with respect to the longitudinal portion respectively. With such architecture, whatever the robot positioning, each electrical motor of the system activate a movement, which corresponds to a right/left, up/down or in/out movements of the endoscope respectively. The right/left and up/down movements are the two rotations enabling the viewing of the entire abdominal cavity, whereas the in/out movement is a translation displacing the endoscope closer to or further from the organs of interest.

Any order given by the surgeon, for instance by voice or foot, directly actuates one motor which moves the endoscope according to the required movement. One advantage of such a system is that it does not require any computer calculation for moving the endoscope. The system is thus very simple to use and configure but this also create artifacts in the movement depending on the current position of the endoscope. When moving a camera, right/left movement for the user corresponds to moving the camera field on the right or left side of the field of view in a direction perpendicular to the up/down direction of the image. Due to the arrangement of the elements of the system, orientation of endoscope axis with respect to right/left movement axis is modified by up/down movement. When the rotation axis is not perpendicular to the longitudinal axis of the endoscope, then the movement due to the rotation around such rotation axis is not linear on the image but rather makes an arc which creates the above mentioned artifacts in the visualisation given to the surgeon.

A goal of the present invention is to propose a simple and easy to use system for controlling displacement of an intervention device, in particular an endoscope, that addresses the above mentioned drawbacks.

In particular, a goal of the present invention is to propose a simple and easy to use system for controlling displacement of an intervention device, in particular an endoscope, that gives accurate information to the surgeon during his surgery.

SUMMARY OF THE INVENTION

To this end, is proposed a system as defined in the appended claims for controlling displacement of an intervention device.

Preferably, it is proposed a system for controlling with respect to a body of a patient, displacement of an intervention device having an end intended to be inserted in the body of the patient through a point of penetration, comprising:

A base intended to be in a fixed position relative to the patient;

A first portion comprising an arc member, said first portion being pivotally mounted on the base around a first axis ($A1$), wherein said first axis ($A1$) is parallel to an arc plane defined by the arc member;

A second portion comprising a support member and a carrier member, said support member having a longitudinal axis and said carrier member being slidably mounted on the arc member for partially rotating around a second axis ($A2$), said second axis ($A2$) extending through a centre of curvature of the arc member perpendicularly to the arc plane, wherein the second axis ($A2$) and the first axis ($A1$) are perpendicular;

A third portion comprising
 a holding member for releasable attachment of the intervention device, and
 a sliding member slidably mounted on the support member along a translation axis ($A_T$) being parallel to the arc plane and corresponding to the longitudinal axis of the support member, the holding member being arranged relative to the sliding member so that translation of the sliding member along the translation axis ($A_T$) causes the intervention device to translate along a third axis (A3), and
wherein the first (A1), second (A2) and third (A3) axes are concurrent, the third axis (A3) being parallel to and offset from the translation axis ($A_T$), said offset being made along at least a first offset direction being perpendicular to the translation axis ($A_T$) and parallel to the arc plane, so that when the carrier member is positioned halfway of the arc member then the first (A1), second (A2) and third (A3) axes are orthogonal.

Preferable but not limited aspects of such system, taken alone or in combination, are the following:
- the third axis (A3) is further offset from the translation axis ($A_T$) along a second offset direction perpendicular to the translation axis ($A_T$) and perpendicular to the arc plane.
- the translation axis ($A_T$) is contained within the arc plane without being along a radius of the arc member (21).
- the third axis (A3) is offset so as to have a projection in the arc plane along a radius of the arc member.
- the projection of the third axis (A3) in the arc plane and a radius of the arc member passing through the carrier member defines an offset angle, said offset angle (a) being an angle comprised between 20° and 50°, preferably between 30° and 40°, and more preferably an angle of 35°.
- according to the first offset direction, the third axis (A3) is offset away from the base.
- the holding member is offset relative to the sliding member along a direction parallel to the translation axis (A3) toward the centre of curvature of the arc member.
- the carrier member is the sole coupling between the first portion and the second portion.
- the base comprises an arm designed for positioning of the system relative to the patient in the fixed position where the first axis (A1) is within a plane parallel to the sagittal plane of the patient.
- the base has a design enabling its fixation relative to the patient where the first axis (A1) is inclined relative to a frontal plane of the patient.
- the first axis (A1) is inclined relative to the frontal plane of the patient of an angle ($\beta$) comprised between 25° and 45°, and preferably an angle of 35°.
- the arc member is non-symmetrical relative to any axis within the arc plane being orthogonal to the first axis (A1).
- the arc member has an angular length enabling an angular displacement of the carrier member of an angle comprised between 50° and 90°, and preferably an angle of 70°.
- the arc member has a radius of curvature comprised between 7 cm and 13 cm.
- the system further comprises:
  - A first actuator positioned on the base for actuating rotation of the first portion relative to the base around the first axis (A1);
  - A second actuator positioned on the second portion for actuating sliding of the carrier member on the arc member, for rotation of the carrier member around the second axis (A2);
  - A third actuator positioned on the third portion for actuating sliding of the third portion relative to the support member, for translation of the intervention instrument along the third axis (A3).
- the system further comprises a positioning member releasably attached to the base, and having a positioning end for materialising the point of penetration in the patient.
- the positioning end is within a plane tangent to the patient body in a position offset from the concurring centre of the first (A1), second (A2) and third (A3) axes.

BRIEF DESCRIPTION OF THE DRAWINGS

Other characteristics and advantages of the invention will become clear from the following description which is only given for illustrative purposes and is in no way limitative and should be read with reference to the attached drawings on which.

DETAILED DESCRIPTION OF THE INVENTION

The description below is made in reference to the control of the displacement of an endoscope which is of main use in the minimally invasive surgeries, but it is applicable to the control of the displacement of any intervention device by a holder.

In this description, two axes are said to be perpendicular when they are coplanar and concurrent and form an angle of 90°.

Further, two axes being perpendicular are orthogonal. The reciprocal is not true as two orthogonal axes are not necessarily coplanar and concurrent.

Three axes are said to be perpendicular when the axes are all orthogonal to one another and concur at a same point.

The proposed system enables control, with respect to a body of a patient, of the displacement of an intervention device having an end intended to be inserted in the body of the patient through a point of penetration, e.g. an endoscope. More precisely, such system enables the endoscope to be rotated around two rotation axes in order to create the left/right and up/down movements respectively, and to be translated along another axis in order to create the in/out movement corresponding to the zoom function of the endoscope.

The proposed system, also referred to a holder in the following description, has a particular arrangement made so that the three axes defining the two rotations and the translation of the endoscope are perpendicular when the system is in its centre of range of motion. This position where the three axes are perpendicular is the optimal position with regard to the accuracy of the image given by the endoscope as there are no artifacts in the movements around that position.

The proposed system thus ensures that the optimal position of the intervention device with respect to the system is the main position around which the intervention device is displaced. The closer the endoscope to the optimal position, the more accurate the movement looks like for the surgeon.

Figure 1:
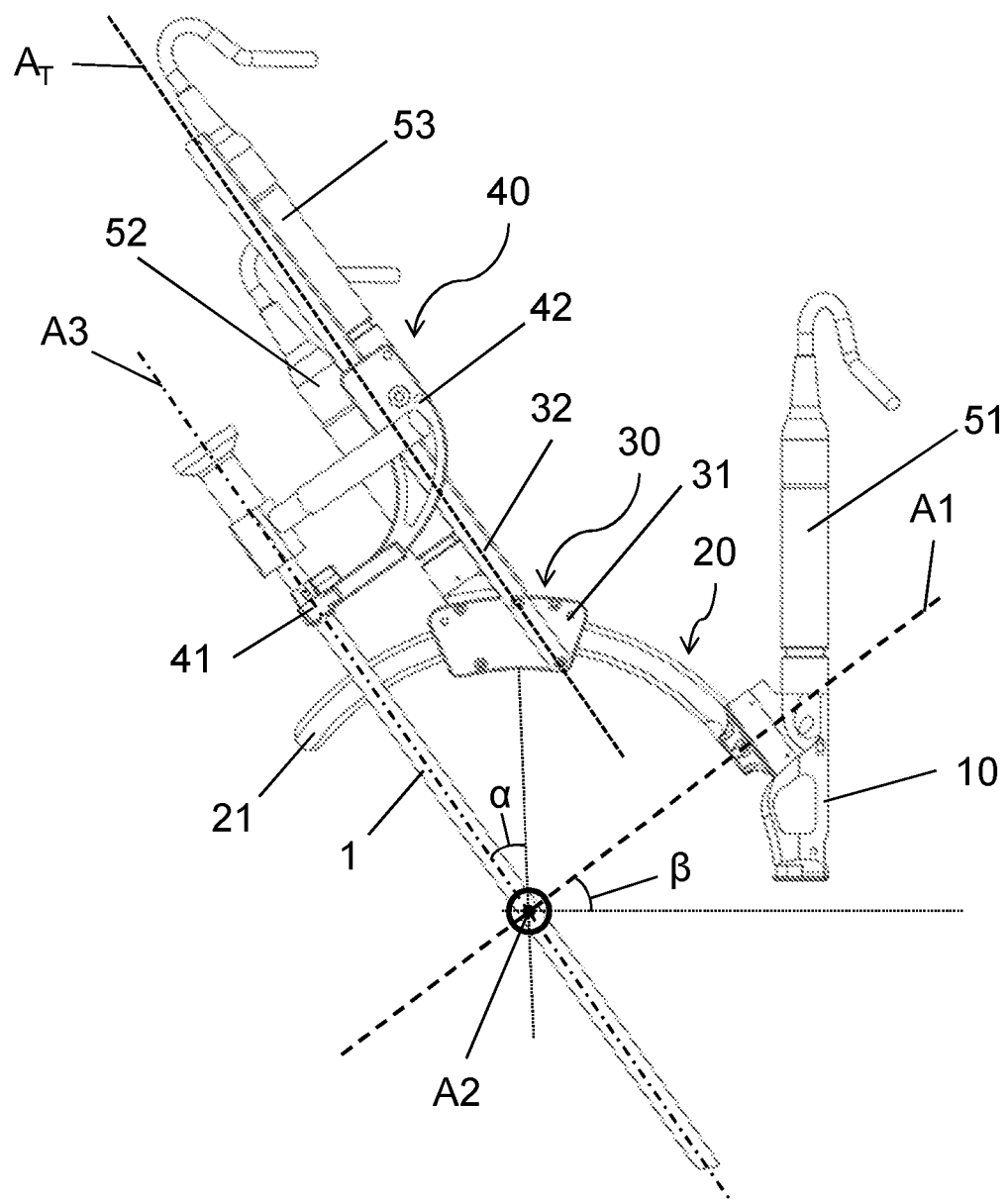
FIG. 1 is a schematic representation of the proposed system for controlling displacement of an intervention device, in the intermediate operating position of the system.

FIG. 1 illustrates an embodiment of the proposed system in such optimal position where all axes of displacement of the intervention device 1 are orthogonal.

The system comprises a base 10 which is intended to be in a fixed position relative to the patient.

To this end, the system can be coupled to a passive arm configured and positioned to hold the system just above the patient, for instance close to the abdomen. This passive arm can be attached to the operative table, using for instance the rail provided in the operating table. Alternatively, it can be attached to a structure that lay on the floor.

For easing the positioning of the holder relative to the patient, the base 10 is preferably attached to the passive arm with a fast release system.

The holder, as well as the passive arm, are preferably submersible and autoclavable.

The proposed system further comprises a first portion 20 comprising an arc member 21. This first portion 20 is pivotally mounted on the base 10 around a first axis A1, wherein said first axis A1 is parallel to an arc plane defined by the arc member 21. Preferably the first axis A1 does not belong to the arc plane.

The first portion 20 may be mounted on the base 10 so that one end of the arc member 21 intersects the projection of first axis A1 in the arc plane.

Preferably, the first portion 20 comprises a surface configured to engage with the drive gear of a first actuator 51 provided on the base 10. The first actuator 51 enables controlling the rotational movement of the first portion 20 with respect to base 10 around the first axis A1, also called first pivot axis.

Preferably for abdominal surgery with patient lying on the back, the first pivot axis A1 forms with the frontal plane of the patient that lies on the surgical table an angle (β) comprised between 25° and 45°, and preferably an angle of 35°. This angle β is referred to the inclination angle β.

Such inclination of the first axis relative to the frontal plane of the patient is particularly advantageous as it gives an optimal operational range of the endoscope while improving the compactness of the holder.

Preferably the first portion 20 is mounted on the base 10 in a manner to create such inclined first axis A1. Alternatively, such inclination of the first axis A1 relative to the frontal plane of the patient is made by specifically positioning the base 10 relative to the patient with the passive arm.

The operational axis of the first actuator 51 can be collinear to the first pivot axis A1. In another embodiment as illustrated in FIG. 1, the operational axis of the first actuator 51 can be angled relative to the first pivot axis A1. Preferably the operational axis of the first actuator 51 is perpendicular to a plane tangent to the patient's body, with a specific gear mechanism to transmit the movement to the first axis A1. This has the advantage of reducing the overall foot print of the system on the patient's body. For an abdominal surgery with the patient lying on the back, the plane tangent to the patient's body is defined as the plane parallel to the frontal plane of the patient body and tangent to abdominal skin.

The arc member 21 of the first portion 20 defines an arc of a circle around an axis being perpendicular to the first pivot axis A1.

The system further comprises a second portion 30 comprising a support member 32 and a carrier member 31.

The carrier member 31 is slidably mounted on the arc member 21 which defines a rotation movement around a second axis A2. This second axis A2, also called second pivot axis, extends through the centre of curvature of the arc member 21 perpendicularly to the arc plane.

By construction, the second axis A2 and the first axis A1 are perpendicular.

Preferably, the second portion 30 is coupled to a second actuator 52. The first portion 20, particularly the arc member 21, comprises a surface configured to engage with the drive gear of the second actuator 52.

The second actuator 52 enables controlling the rotational movement of the second portion 30 with respect to the arc member 21 of the first portion 20 around the second axis A2.

Preferably, the carrier member 31 sliding on the arc member 21 is the sole coupling between the first portion 20 and the second portion 30.

The system also comprises a third portion 40 that includes a sliding member 42 slidably mounted on the support member 32 of the second portion 30 along a translation axis $A_T$ being parallel to the arc plane.

Preferably the support member 32 has a longitudinal shape and the translation axis $A_T$ corresponds to the longitudinal axis of the support member 32.

In this case, the sliding member 42 can be mounted around the support member 32 to translate along the support member 32.

The support member 32 can for instance be a shaft, having preferably a non-circular cross-section so that it further acts as a guide for the translation of the sliding member 42.

The third portion 40 also includes a holding member 41 for releasable attachment of the intervention device 1.

Preferably, the holding member 41 comprises a fast release system so that the intervention device 1 can be detached from the system at any time.

The holding member 41 of the third portion 40 is arranged relative to the sliding member 42 so that translation of the sliding member 42 along the translation axis $A_T$ causes the intervention device to translate along a third axis A3. The third axis A3 is thus an axis parallel to the translation axis $A_T$ and different from it. Preferably, the third axis A3 passes through the intervention device 1 when it is mounted on the holding member 41.

The third portion also preferably comprises a third actuator 53. The support member 32 of the second portion 30 can have a surface configured to engage with the drive gear of the third actuator 53.

The third actuator 53 enables controlling the translation movement of the third portion 40 with respect to the second portion 30 along the translation axis $A_T$, which thus controls the translation movement of the intervention device 1 along the third axis A3, which preferably corresponds to the longitudinal axis of the intervention device 1.

The system has a specific arrangement where the first axis A1, the second axis A2 and the third axis A3 are always concurrent.

The third axis A3 is parallel to and offset from the translation axis $A_T$, said offset being made along a first offset direction being perpendicular to the translation axis $A_T$ and parallel to the arc plane so that when the carrier member 31 is positioned halfway of the arc member 21 then the first axis A1, the second axis A2 and the third axis A3 are orthogonal.

By construction, the longitudinal axis of the intervention device is perpendicular to the second pivot axis A2 whatever the position of the system. Moreover the system is designed so that when the carrier member 31 is in the centre of its range of movement on the arc member 21, the device longitudinal axis is also perpendicular to the first pivot axis A1.

Preferably, the third axis A3 is also offset from the translation axis $A_T$ along a second offset direction perpendicular to the translation axis $A_T$ and perpendicular to the arc plane. In particular, when the translation axis $A_T$ is not contained within the displacement plane of the intervention device, such offset enables offsetting the third axis A3 in such displacement plane. By displacement plane is meant the plane within which the intervention device 1 is intended to be displaced, defined by the first pivot axis A1 and the longitudinal axis of the intervention device 1.

The offsets are defined so that the first axis A1, the second axis A2 and the third axis A3 are always concurrent.

Preferably, the third axis A3 is offset away from the base 10, along the first offset direction.

The fact that the third axis A3 is offset from the translation axis $A_T$ enables offsetting the longitudinal axis of the intervention device 1 from the free end of the arc member 21.

Figure 3:
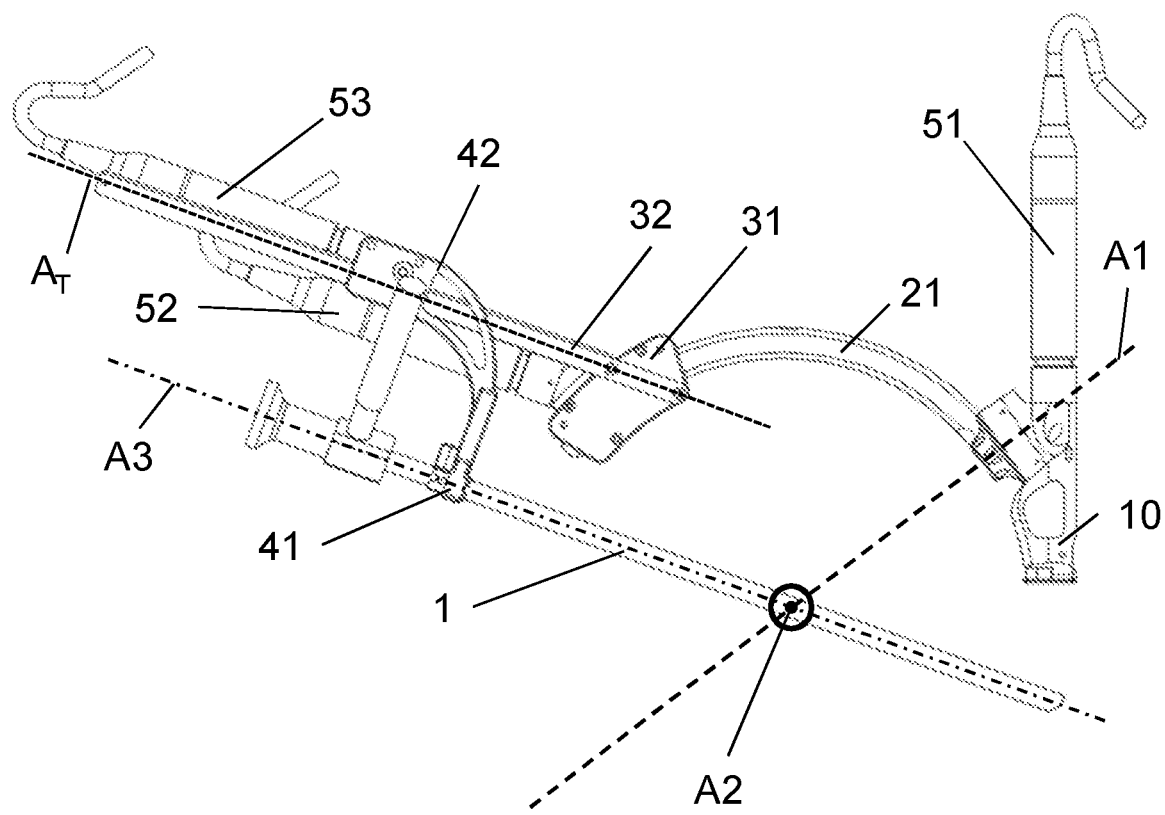
FIG. 3 is a schematic representation of the system of FIG. 1, illustrating the other extreme position in the up/down movement of the intervention device, i.e. the maximum up position of the end of the intervention device within the patient.

Indeed, with this arrangement, when the carrier member 31 is at the end of the arc member 21 as illustrated in FIG. 3, the longitudinal axis of the intervention device 1 forms a smaller angle with the plane tangent to patient's body than a radius passing through the carrier member 21.

With such an arrangement, the arc member 21 can be made shorter so that it does not get in conflict with the patient's body when pivot movement around the first axis A1 is actuated, without affecting the range of motion of the intervention device 1.

Preferably, the arc member 21 is non-symmetrical relative to any axis within the arc plane being orthogonal to the first axis A1, which further participates to the compactness of the holder. In particular, such arrangement enables the arc member 21 to have an angular length lower than 180°. Preferably, the angular length of the arc member 21 is lower than 120°, and more preferably comprised between 60° and 100°. This is particularly advantageous as it prevents the arc member 21 from intersecting the body of the patient when the system is operated.

In this arrangement, as the third axis A3 is oriented as a radius of the arc member 21 to make the three axes A1, A2 and A3 concurrent, the translation axis $A_T$ is preferably not perpendicular to the tangent of the arc member 21, and thus not oriented as a radius of the arc member.

Preferably, the projection of the third axis A3 in the arc plane and a radius of the arc member 21 passing through the carrier member 31 defines an offset angle α which is comprised between 20° and 50°, preferably between 30° and 40°, and more preferably an angle of 35°.

The arc member 21 can have an angular length enabling an angular displacement of the carrier member 31 of an angle comprised between 50° and 90°, and preferably an angle of 70°.

Figure 2:
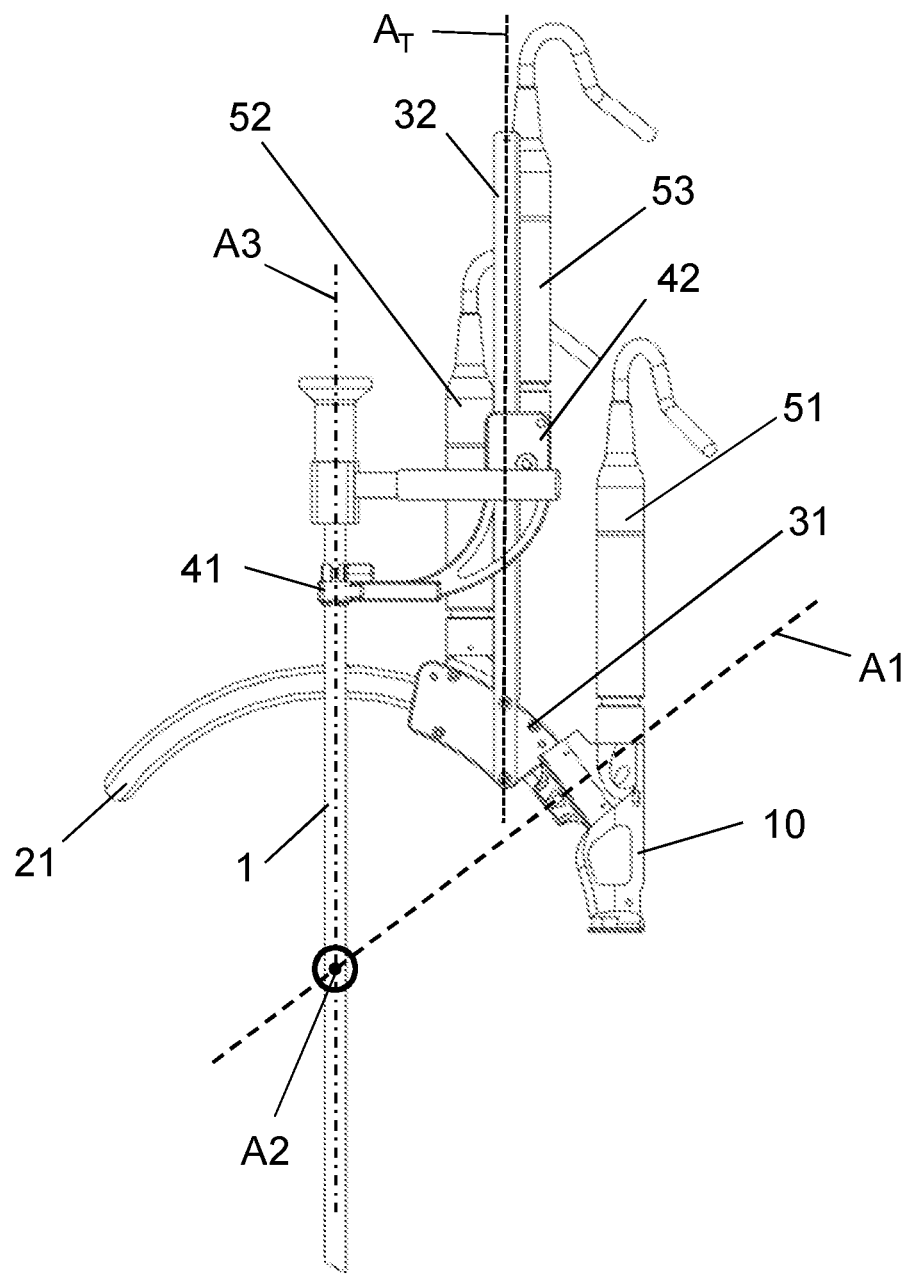
FIG. 2 is a schematic representation of the system of FIG. 1, illustrating one extreme position in the up/down movement of the intervention device, i.e. the maximum down position of the end of the intervention device within the patient.

FIGS. 2 and 3 represent the extreme positions in the up/down movement of the system actuated by the rotation of the carrier member 31 around the second axis A2. More precisely, FIG. 2 illustrates the maximum down position of the intervention device where the carrier member 31 is close to the base 10. FIG. 3 illustrates the maximum up position of the intervention device, where the carrier member 31 is positioned at the free end of the carrier member 21.

Preferably the holder is arranged so that at the maximum down position of the intervention device, the intervention device 1 is positioned so that its longitudinal axis is perpendicular to a plane tangent to the patient's body as illustrated on FIG. 2.

As illustrated on FIG. 3, the holder is further preferably arranged so that at the maximum down position, the longitudinal axis of the intervention device 1 forms an angle relative to the plane tangent to the patient's body comprised between 10° and 30°, preferably an angle of 20°.

According to a preferred embodiment, the arc member 21 has an angular length enabling an angular displacement of the carrier member 31 of 70°, the projection angle α is of 35°, and the inclination angle β is also of 35°.

The holder is then arranged so that at the maximum up position, the intervention device 1 is positioned so that its longitudinal axis is perpendicular to the plane tangent to the patient's body, and that at the maximum down position, the longitudinal axis of the intervention device 1 forms an angle relative to the plane tangent to the patient's body of 20°.

In such configuration, in the intermediate position illustrated in FIG. 1 where the carrier member 31 is at its centre range of motion, the longitudinal axis of the intervention device 1 forms an angle relative to the plane tangent to the patient's body of 55°.

The arc member 21 is not in the plane defined by first pivot axis A1 and the longitudinal axis of the intervention device in order to ease the operation and movement of the intervention device 1.

When the translation axis $A_T$ is not within the plane defined by first pivot axis A1 and the longitudinal axis of the intervention device, the offset of the third axis A3 from the translation axis $A_T$ along the second offset direction perpendicular to the translation axis $A_T$ and perpendicular to the arc plane enable the third axis A3 to be perpendicular to first axis A1 and second axis A2.

For example, the distance between longitudinal axis of the intervention device 1 and the arc member along the second offset direction is between 1 cm and 2.5 cm.

In the embodiments illustrated in the figures, the first portion 20 comprises a single arc member 21. However, according to another embodiment, the first portion 20 comprises two similar arc members arranged on each side of the displacement plane of the intervention device 2.

In a general manner, the mechanical components forming the holder are made so that the holder is confined in a volume above the plane P tangent to patient's body.

Figure 5:
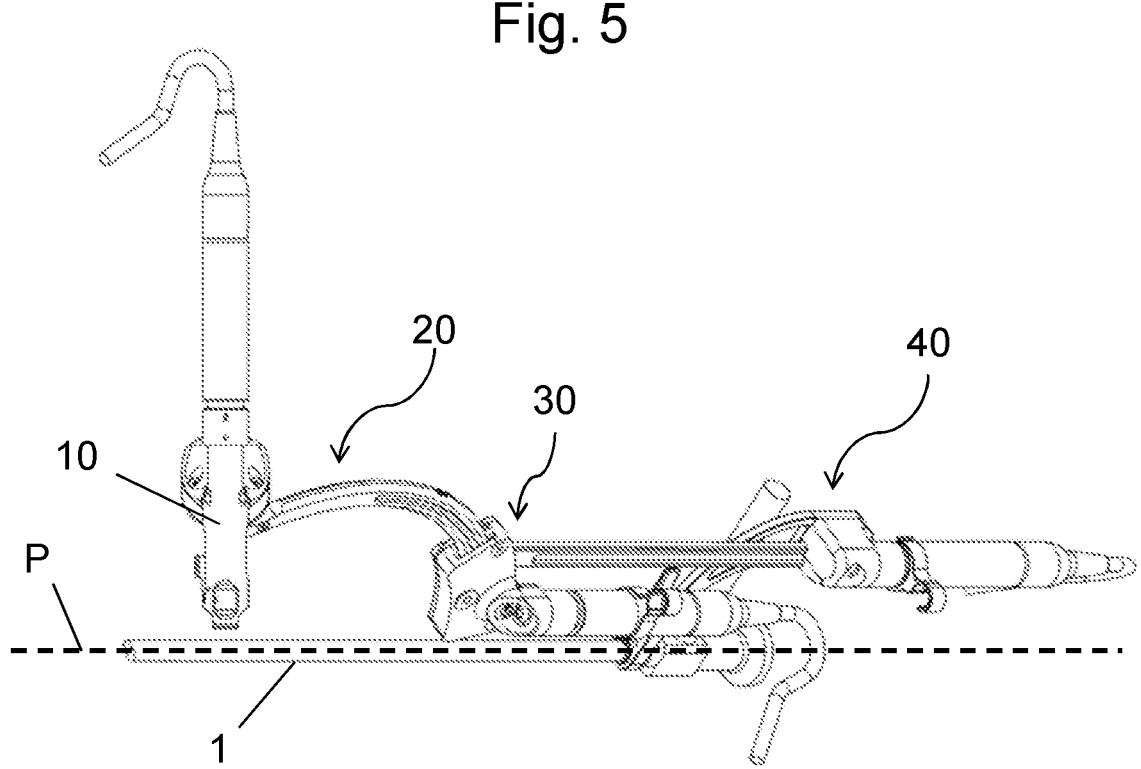
FIG. 5 is a schematic representation of the system of FIG. 1, illustrating one extreme position in the left/right movement of the intervention device, i.e. the maximum right position of the end of the intervention device within the patient.
Figure 6:
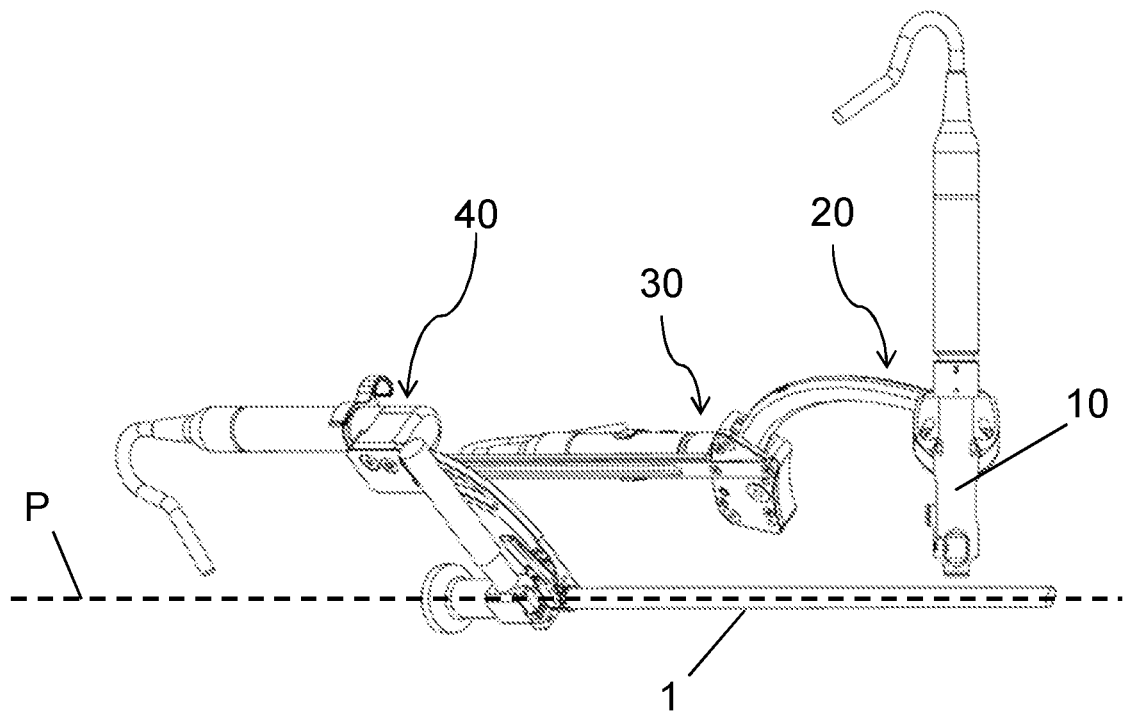
FIG. 6 is a schematic representation of the system of FIG. 1, illustrating the other extreme position in the left/right movement of the intervention device, i.e. the maximum left position of the end of the intervention device within the patient.

This is illustrated in particular in FIGS. 5 and 6 that represent the holder when the intervention device 1 is in the extreme up position explained above, and in the extreme right position and extreme left position respectively.

One advantage of the proposed design for the holder is that its compactness enables a positioning of the system relative to the patient in a fixed position where the first axis A1 is within a plane parallel to the sagittal plane of the patient. This is particularly advantageous for positioning and displacing an endoscope in the abdomen of a patient, or for positioning and displacing a uterine manipulator for example.

In case the intervention device is a laparoscopic instrument, it is inserted in the patient body through a cannula.

A cannula is composed of a hollow cylinder body that is inserted in the patient abdomen and a head that stays outside patient's body and comprises valves to maintain pneumoperiteum both when device is in the cannula and when it is not.

Depending on the abdominal wall thickness and the surgical indication, the cannula is more or less inserted in the patient body. In any case the arc member 21 of the system must be designed to leave enough space for the part of the cannula outside the patient's body.

Preferably, the arc member 21 radius is large enough to leave enough space underneath for the cannula, but not too large to limit the system footprint on the patient's body.

Preferably, the arc member 21 has a radius of curvature comprised between 7 cm and 13 cm.

As mentioned above, the third portion 40 is designed to offset the third translation axis A3, and thus the intervention device 1, in a first direction away from the base 10. This also enables providing space for the cannula between the device and the arc member 21.

For example, the distance between the longitudinal axis of the device and the translation axis $A_T$ of the third portion is comprised between 2.5 cm and 5 cm.

Figure 4:
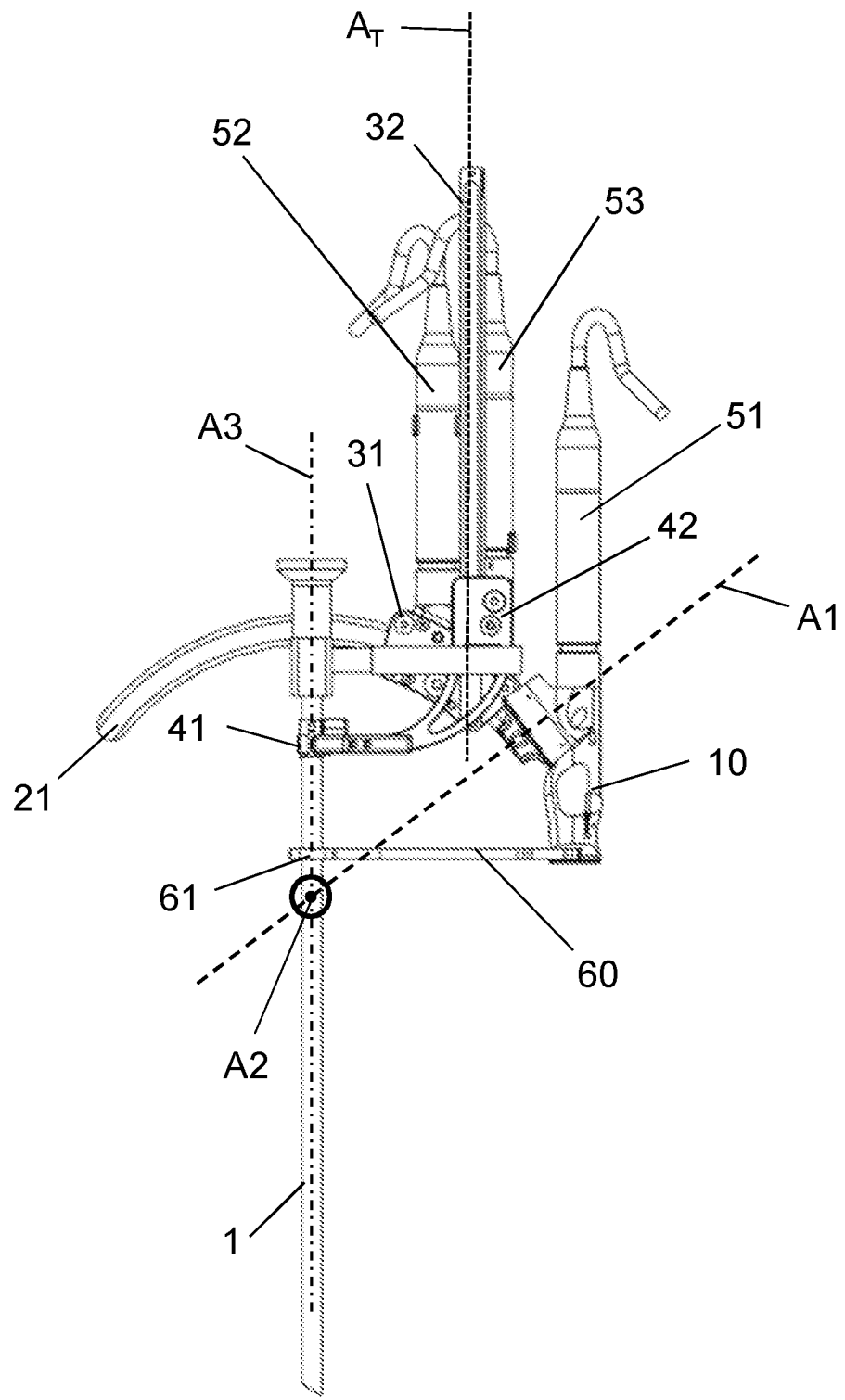
FIG. 4 is a schematic representation of the system of FIG. 1, illustrating one extreme position in the in/out movement of the intervention device, i.e. the maximum in position of the intervention device.

In one preferred embodiment, the holding member 41 is offset relative to the sliding member 42 along a direction parallel to the translation axis A3 toward the centre of curvature of the arc member 21, so that the device can be inserted further in the patient. Indeed, as illustrated in FIG. 4, the holding member 41 used to attach the intervention device 1 is closer to the penetration point (e.g. skin of the patient) than the carrier member 31 which remains along the arc member 21.

In case the intervention device 1 is an endoscope, the rotation around the first pivot axis A1 corresponds to the video image right/left movement and the rotation around the second pivot axis A2 corresponds to video image up/down movement.

By construction, the longitudinal axis of the endoscope is orthogonal to the second pivot axis A2 whatever the position of the system. The rotation around the second pivot axis A2 thus always creates a perfect up/down movement in the video image frame.

When the longitudinal axis of the endoscope is orthogonal to the first pivot axis A1, then the rotation around the first pivot axis A1 creates a perfect right/left movement in the video image. As mentioned above, this position corresponds to the centre of the range of motion around the second axis A2.

With the arrangement of the proposed system, the endoscope is moved around this central position such that the video image frame is only minimally degraded when moved around this position.

Preferably, the range of motion of the intervention device is substantially symmetrical with respect to the central position, in particular with regard to the up/down and left/right movements.

The first 51, second 52 and third 53 actuators are preferably electric motors but could also be operated manually. They can also be disengageable motors that may be operated manually only when required.

In another embodiment the actuators can also be braking system (friction, electromagnetic . . . ). In particular in the case where displacement of the device is done manually, the actuators enable holding the device in a fixed position.

Preferably, the holder is connected to a console which contains motion controllers and software. It analyses the orders of the surgeon and translates them to low level motor commands.

Such console can comprise a touch panel screen as a user interface (robot and voice settings) and a front panel containing connectors for the different command modes (footswitch or wireless microphone) and the motorized scope holder.

The system can be controlled either by voice (e.g. through a microphone supervised by a single footswitch for security) or by foot (e.g. through a footswitch).

In a preferred embodiment, the actuators include coders, so that the position of the intervention device 1 can be tracked precisely.

According to a particular embodiment, the console comprises a control unit that is adapted for positioning the intervention device to a specific position, for instance a position saved in advance.

According to an embodiment of the invention, the intervention device 1 is connected to the holding member 41 of the third portion with a connection with one degree of freedom to allow for rotation of the device along its own longitudinal axis. This embodiment is particularly advantageous when the intervention device 1 is an endoscope as the user may need to rotate the endoscope around its longitudinal axis.

According to another embodiment of the invention, the holding member 41 of the third portion is designed to securely fasten the intervention device 1, without any degree of freedom between the intervention device 1 and the holding member 41. This embodiment is particularly advantageous when the intervention device 1 is a uterine manipulator for instance, where it has to be firmly held in position.

Such coupling may for instance be made with a ring adapter. The material of this ring adapter is chosen to create friction with the device so that device cannot pivot along its longitudinal axis under its own weight, but can be pivoted along its longitudinal axis by human actuation.

In another embodiment, this degree of freedom is controlled by a fourth actuator.

To facilitate positioning of the system with respect to the point of penetration through which the device is inserted, a positioning mechanical part 60 is attached to the base 10 to materialize the point of concurrence of the two pivot axes and the device longitudinal axis.

More precisely, the practitioner will use the free end the positioning part 60 to materialize the position of said point of concurrence. Such free end is referred to positioning end 61.

Preferably, the end of the positioning part 60 is slightly offset from the theoretical point of concurrence. This is particularly advantageous when the point of concurrence shall not be flush with the surface of the skin of the patient but rather slightly inside the patient (e.g. slightly under the surface of the skin). In this latter case, the practitioner can namely position the system by placing the positioning end 61 flush with the surface of the skin at the point of penetration.

Preferably this positioning part 60 can be released from base 10 when system is positioned and passive arm locked to maintain the base 10 in place.

The above detailed description has been mainly made in reference to an intervention device having a longitudinal shape, as is the case in an endoscope, but the corresponding teachings could be applied to any other shape of such intervention device. In such case, the above mentioned longitudinal axis of the intervention device would correspond to the translation axis of displacement to perform the in/out movement of the device (corresponding to the zoom-in/zoom-out function for an endoscope).

BIBLIOGRAPHIC REFERENCES

U.S. Pat. No. 8,591,397

The invention claimed is:

1. A system for controlling with respect to a body of a patient, displacement of an intervention device having an end intended to be inserted in the body of the patient through a point of penetration, comprising:
A base intended to be in a fixed position relative to the patient;
A first portion comprising an arc member, said first portion being pivotally mounted on the base around a first axis, wherein said first axis is parallel to an arc plane defined by the arc member;
A second portion comprising a support member and a carrier member, said support member having a longitudinal axis and said carrier member being slidably mounted on the arc member for partially rotating around a second axis, said second axis extending through a centre of curvature of the arc member perpendicularly to the arc plane, wherein the second axis and the first axis are perpendicular;
A third portion comprising
a holding member for releasable attachment of the intervention device, and
a sliding member slidably mounted on the support member along a translation axis being parallel to the arc plane and corresponding to the longitudinal axis of the support member,
the holding member being arranged relative to the sliding member so that translation of the sliding member along the translation axis causes the intervention device to translate along a third axis, and
wherein the first, second and third axes are concurrent, the third axis being parallel to and offset from the translation axis, said offset being made along at least a first offset direction being perpendicular to the translation axis and parallel to the arc plane, so that when the carrier member is positioned halfway of the arc member then the first, second and third axes are orthogonal, and wherein the third axis is offset so as to have a projection in the arc plane along a radius of the arc member, wherein said projection of the third axis in the arc plane and a radius of the arc member passing through the carrier member define a non-zero offset angle.

2. The system of claim 1, wherein the third axis is further offset from the translation axis along a second offset direction perpendicular to the translation axis and perpendicular to the arc plane.

3. The system of claim 1, wherein the translation axis is contained within the arc plane without being along a radius of the arc member.

4. The system of claim 1, wherein the offset angle is an angle comprised between 20° and 50°.

5. The system of claim 1, wherein according to the first offset direction, the third axis is offset away from the base.

6. The system of claim 1, wherein the holding member is offset relative to the sliding member along a direction parallel to the translation axis toward the centre of curvature of the arc member.

7. The system of claim 1, wherein the carrier member is the sole coupling between the first portion and the second portion.

8. The system of claim 1, wherein the base comprises an arm designed for positioning of the system relative to the patient in the fixed position where the first axis is within a plane parallel to the sagittal plane of the patient.

9. The system of claim 1, wherein the base has a design enabling its fixation relative to the patient where the first axis is inclined relative to a frontal plane of the patient.

10. The system of claim 9, wherein the first axis is inclined relative to the frontal plane of the patient of an angle comprised between 25° and 45°.

11. The system of claim 9, wherein the first axis is inclined relative to the frontal plane of the patient of an angle of 35°.

12. The system of claim 1, wherein the arc member is non-symmetrical relative to any axis within the arc plane being orthogonal to the first axis.

13. The system of claim 1, wherein the arc member has an angular length enabling an angular displacement of the carrier member of an angle comprised between 50° and 90°.

14. The system of claim 1, wherein the arc member has a radius of curvature comprised between 7 cm and 13 cm.

15. The system of claim 1, comprising:
A first actuator positioned on the base for actuating rotation of the first portion relative to the base around the first axis;
A second actuator positioned on the second portion for actuating sliding of the carrier member on the arc member, for rotation of the carrier member around the second axis;
A third actuator positioned on the third portion for actuating sliding of the third portion relative to the support member, for translation of the intervention device along the third axis.

16. The system of claim 1, further comprising a positioning member releasably attached to the base, and having a positioning end for materialising the point of penetration in the patient.

17. The system of claim 16, wherein the first, second and third axes are concurrent at a concurring centre, the positioning end being within a plane tangent to the patient body in a position offset from the concurring centre of the first, second and third axes.

18. The system of claim 1, wherein the offset angle is an angle comprised between 30° and 40°.

19. The system of claim 1, wherein the offset angle is an angle of 35°.

20. The system of claim 1, wherein the arc member has an angular length enabling an angular displacement of the carrier member of an angle of 70°.

* * * * *